United States Patent [19]

Roberts, Jr.

[11] 4,208,906
[45] Jun. 24, 1980

[54] MUD GAS RATIO AND MUD FLOW VELOCITY SENSOR

[75] Inventor: Liona R. Roberts, Jr., La Habra, Calif.

[73] Assignee: Interstate Electronics Corp., Anaheim, Calif.

[21] Appl. No.: 903,801

[22] Filed: May 8, 1978

[51] Int. Cl.$^2$ ............................................ E21B 47/00
[52] U.S. Cl. ........................................ 73/155; 73/597; 364/422
[58] Field of Search ................. 73/597, 155; 181/102; 364/422, 804

[56] References Cited

U.S. PATENT DOCUMENTS

| | | | |
|---|---|---|---|
| 2,806,372 | 9/1957 | Arps . | |
| 3,103,812 | 9/1963 | Bourne, Jr. et al. | 73/155 |
| 3,580,092 | 5/1971 | Scarps | 73/194 |
| 3,603,145 | 9/1971 | Morris | 73/155 |
| 3,646,808 | 3/1972 | Leonard | 73/155 |
| 3,710,615 | 1/1973 | Johnson et al. | 73/61 R |
| 3,750,766 | 8/1973 | Thompson et al. | 175/50 |
| 3,760,891 | 9/1973 | Gadbois | 175/48 |
| 3,821,726 | 6/1974 | Chang et al. | 340/239 R |
| 3,839,914 | 10/1974 | Modisette et al. | 73/438 |
| 3,861,211 | 1/1975 | Dewan | 73/194 A |
| 3,901,078 | 8/1975 | McShane | 73/194 A |
| 3,906,780 | 9/1975 | Baldwin | 73/61 R |
| 3,910,110 | 10/1975 | Jefferies et al. | 73/155 |
| 3,954,008 | 5/1976 | Yamamoto et al. | 73/194 A |
| 3,982,432 | 9/1976 | Hammond | 73/151.5 |
| 4,003,256 | 1/1977 | Donelan et al. | 73/194 A |
| 4,080,837 | 3/1978 | Alexander et al. | 73/597 X |
| 4,109,523 | 8/1978 | Teyssandier | 73/194 A |
| 4,112,735 | 9/1978 | McKnight | 73/19 |
| 4,114,438 | 9/1978 | Muraz et al. | 73/194 A |
| 4,114,439 | 9/1978 | Fick | 73/194 A |

Primary Examiner—Jerry W. Myracle
Attorney, Agent, or Firm—Knobbe, Martens, Olson, Hubbard and Bear

[57] ABSTRACT

A remote sensor for the measurement of the amount of gas present in the drilling fluid or "mud" in an offshore well-drilling operation, for the purpose of giving prompt warning of geologic conditions conducive to the occurrence of a blow-out. An acoustic projector projects an acoustic wave of fixed wavelength through the mud returning upwardly from the borehole. The wave is received by a first array of acoustic receivers locked in a known phase relationship with the projector. Changes in the speed of sound due to changing relative amounts of mud and gas produce a shift in frequency of the acoustic wave which is proportional to the speed of sound in the mud/gas mixture. The change in frequency is electronically detected and scaled to yield the value of the speed of sound, from which the mud to gas mass ratio is calculated by means of a computer. A second array of acoustic receivers is arranged with the first array and the projector to form a phase-shift velocimeter which uses the value of the speed of sound obtained in conjunction with the mud/gas mass ratio measurement to calculate the velocity of the mud flow, which is used as a further indicator of potential blowout conditions.

25 Claims, 10 Drawing Figures

$$\gamma = \frac{-B + \sqrt{B^2 - 4AK}}{2A}$$

FIG. 7D.

MUD GAS RATIO AND MUD FLOW VELOCITY SENSOR

BACKGROUND OF THE INVENTION

This invention relates to a remote sensor for detecting and measuring the presence of gas in drilling mud and for measuring the flow velocity of the drilling mud.

In drilling an oil well a drilling fluid known as drilling "mud", is circulated through the drill stem and the bit and into the bore hole to cool and lubricate the bit, to remove drilling debris from the borehole, and to prevent material from entering the well through the bore hole wall. The pressure and the density of the drilling mud is carefully controlled to balance or slightly overbalance the hydrostatic pressure of the earth formations surrounding the bore hole, thereby preventing any fluids which may be trapped in these surrounding earth formations from entering the bore hole. There exits a danger, however, that the drill may enter an earth formation in which abnormally high geopressures are present. In such a situation, the geopressures of the formaton will overbalance the opposing hydrostatic pressure of the drilling mud, thereby permitting the entrapped fluids in the formation to enter the well. Such an occurrence is termed a "kick". If this situation is not detected and controlled promptly, the drilling mud may be substantially displaced and the highly pressurized fluids may flow freely up the well causing what is known as a "blowout".

A particularly dangerous situation occurs when a drill strikes a formation containing abnormally highly pressurized gas. In such a situation minute bubbles of gas will enter the bore hole of the well and rise up through the mud, expanding as they rise due to the decreasing head of mud above them. As the bubbles expand in the mud, they further reduce the hydrostatic head of the mud column allowing more rapid entry of gas bubbles at the bottom. This situation is cumulative, and, if left unchecked, the hydrostatic pressure of the mud will be reduced to such an extent that there will be no longer any effective barrier against the inrushing gas, and a blowout will result.

The prevention of blowouts is most effectively achieved by promptly detecting the influx of highly pressurized fluid into the well before an appreciable amount of drilling fluid is displaced from the well. It is well-known that by measuring certain properties of the mud returning out of the well, the presence of conditions at the bottom of the well which indicate a blowout potential can be detected. For example, the mud returning from the well to the surface may be analyzed by means of conventional catalytic or "Hot Wire" gas detectors to determine the amount of gas in the mud, known as "gas cutting" of the mud. A relatively sudden and substantial increase in the degree of gas cutting indicates that the drill has struck a formation containing abnormally highly pressurized gas. This would be indicated, for example, by a decrease in the volumetric or mass ratio of mud to gas in the mud returning from the borehole. Additionally, the velocity of returning mud can be measured and compared with the velocity of the mud entering the well. A substantial increase in the velocity of the returning mud with respect to the velocity of the mud entering the well likewise indicates the occurrence of a kick.

While several methods have been discovered for taking measurements for gas cutting and mud flow velocity, such methods contemplate the taking of these measurements at or near the earth's surface or, in the case of off-shore wells, on or near the drilling platform. This presents a significant delay between the time the kick occurs and the time that the measurements can be taken to determine the occurrence of the kick due to the time it takes for the mud to travel from the bottom of the borehole to the location of the measuring apparatus. In relatively shallow wells this delay will only be a few minutes, giving the well operator in most cases sufficient time to take corrective action to prevent the blowout. Such is usually the case, for example, in offshore wells operating in water depths of less than about 30 meters. However, the search for oil has led drilling teams to deeper parts of the ocean where water depths may be several hundred to thousands of meters. In such deep offshore wells, it may take as long as one hour or more for the mud to travel from the ocean floor to the ocean surface. There is, therefore, a very long delay between the time a kick occurs at the bottom of the borehole and the time that the occurrence of the kick can be determined by analyzing the mud at the surface, and this long delay may prevent the operator from taking corrective measures before a blowout occurs.

The present invention remedies this problem by providing means for measuring mud/gas mass ratio and mud flow velocity at the point where the borehole enters the ocean floor. The data obtained from these measurements are processed and transmitted via a data link to a monitoring and control console on board the drilling platform. In this manner, the time delay presented by the traveling of the mud from the ocean bottom to the surface is eliminated, giving the drill operator a much quicker warning of an impending blowout.

SUMMARY OF THE INVENTION

The present invention comprises a system for the remote sensing and measuring of drilling mud properties, particularly mud/gas mass ratio and mud flow velocity.

The theory behind the invention is based upon the behavior of the speed of sound c in a mixture of fluids. For the purposes of this invention both mud and gas may be properly considered fluids since neither will support a shear stress. The speed of sound in mud itself as a fluid is determined largely by its porosity, i.e., the volumetric proportion of interstitial liquid to solid matter. For porosities greater than about 0.5, the speed of sound in mud is almost exactly that of the surrounding liquid. Normal drilling muds with densities up to about twenty pounds per gallon will thus behave as fluids acoustically.

Conceptually, as gas is added to the mud the speed of sound in the mixture will decrease from its nominal value of about sixteen hundred meters per second, since the speed of sound in any gas is much lower than this value. The precise value of the speed of sound in the mud/gas mixture depends upon the type of gas, the temperature and the pressure in a known way and may be determined from the following equation:

$$c^2 = \frac{c_1^2 c_2^2 (\gamma p_2 + p_1)^2}{(1 + \gamma)(\gamma p_2^2 c_2^2 + p_1^2 c_1^2)}$$

where $c_1$ equals the speed of sound in mud, $p_1$ equals the density of the mud, $c_2$ equals the speed of sound in gas, $\rho_2$ equals the density of the gas and $\gamma$ equals the ratio of the mud mass to gas mass.

The quantities $\rho_1$, $\rho_2$, $c_1$, $c_2$ can either be directly measured or deduced from auxiliary measurements. The theory of operation is therefore to measure c and then to compute $\gamma$. Since mud is inherently much more dense than gas even when gas is compressed at the pressures found at depths up to 1,000 meters, the normal operating range for $\gamma$ is about $10^6$ to $10^7$. Values of $10^5$ or lower would represent significant gas cutting of the mud.

The measurement of c is accomplished by acoustical means. An array of acoustical projectors is mounted in a riser extending from the ocean floor to the platform through which the mud returns from the borehole to the platform. The projectors are driven by a voltage controlled oscillator to produce an acoustic wave which propagates within the riser through the mud, and which is received by an array of acoustical receivers located at specific locations within the riser down stream from the projector array. The receiver array consists of one or more pairs of vertically spaced acoustical transducers located with respect to the projector array such that for a given nominal wavelength $\lambda$ and a predetermined number n, the upper receiver is located a distance of $(n+\frac{1}{2})\lambda$ from the phase center of the projector array and the lower receiver is at a distance of $(n-\frac{1}{2})\lambda$ from the phase center of the projector array. Thus, the phase center of the receiver array will be spaced from the phase center of the projector array by a distance R equal to $n\lambda$.

With this arrangement, the output from the receivers will be in a known phase relationship with the input to the projectors if a frequency f is chosen so that given the relationship $f(\lambda/c=1$, $\lambda$ will remain at the value such that $n\lambda = R$. Furthermore, the output will remain in the known phase relationship with the input if, whenever c changes, f is changed accordingly. Therefore, a phase-locked loop is used to drive the voltage controlled oscillator to keep the required relationship between f and c. The resulting frequency is proportional to c since $\lambda$ is a function only of the mechanical spacing of the acoustical components.

By proper scaling, the value of c can be determined, and, using the above relationship between c and $\gamma$, $\gamma$ can be computed.

One particular advantage of the invention is that a phase shift velocimeter may be easily incorporated by providing an additional receiver array in the riser upstream from the projector array. The downstream receiver array is locked into the known phase relationship with the projector array as described above. Due to the velocity of mud, a phase shift is introduced between the upstream array and the downstream array which is proportional to the velocity of the mud and inversely proportional to the accurate value of c which is derived from the mud/gas mass ratio sensor. This value of c is then used in the velocimeter so that the measurement of the velocity of mud may be made with greater accuracy than would be obtainable if the value of c were to be merely estimated.

The acoustical sensor unit is interfaced to a subsurface electronics package which provides the source signal and preprocesses the received outputs. The voltage controlled oscillator powers the projector array. The phase out of the downstream array is compared to the voltage controlled oscillator reference and the voltage controlled oscillator adjusts accordingly to keep the wavelength constant. The resulting frequency is determined, and since it is directly proportional to the speed of sound, approximately scaled to produce c. The phase difference between the upstream and downstream arrays produces the mud speed measurements.

A combination of digital and analogue techniques are used for maximum electrical efficiency, high reliability and adequate accuracy. All outputs are multiplexed onto a signal data link which may also carry other drilling mud data such as temperature, pressure density, etc.

A significant advantage of the mud/gas mass ratio sensor of the present invention is that the measurement of $\gamma$ which it provides can be appropriately scaled to yield an accurate measurement of the gas cutting in conventional units such as milliliters per liter. This is to be compared with present methods of determining gas cutting (such as "hot-wire detectors") which yield only approximate values in arbitrary units such as Canadian Gas Units. Furthermore, this system of the present invention is all electronic and has no mechanical moving parts, and, therefore, no routine maintenance is required beyond calibration.

Another significant advantage of the present invention is the placement of the components of the acoustical sensor unit totally outside of the mud flow in the riser, so that distortions in the measurement of the speed of sound and mud flow velocity are not induced by the turbulence in the mud flow which would result from the placement of the components in the mud flow path.

DETAILED DESCRIPTION OF THE INVENTION

Figure 1:
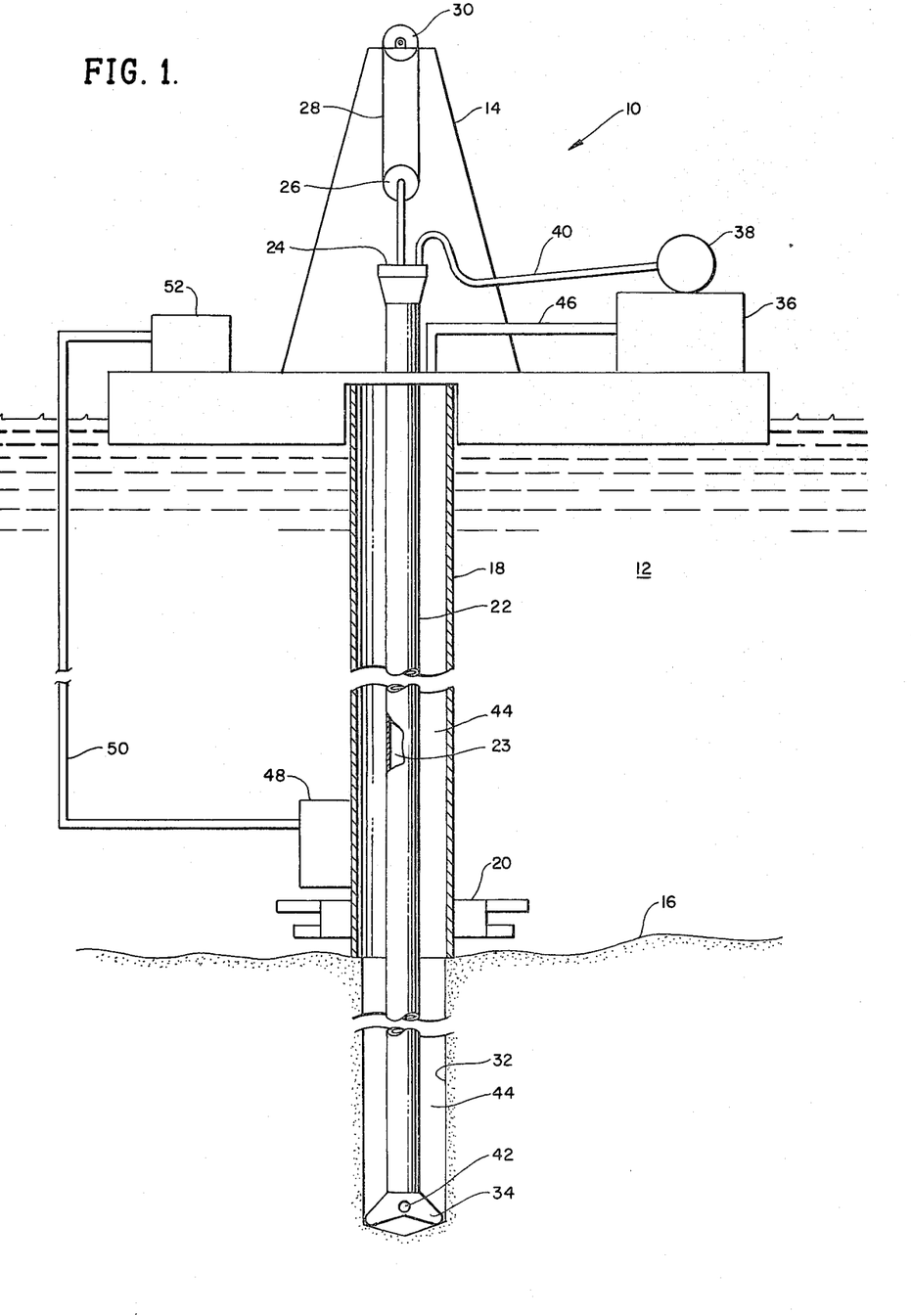
FIG. 1 is a schematic view of an offshore drilling platform and oil well incorporating the present invention.

Referring first to FIG. 1, an offshore drilling platform 10 is shown floating in a relatively deep body of water 12 of a depth of approximately 30 to 1,000 meters. Situated on the platform 10 is a drilling derrick 14 which includes a draw works (not shown) and other apparatus for conducting drilling operations. The body of water 12, which may be considered to be the ocean, has an ocean floor or sea bed 16. A marine riser 18 extends between the platform 10 and the sea bed 16. At the lower end of the riser 18 is a typical blowout preventor stack 20.

A drill stem 22 having a hollow bore 23 is supported from a swivel 24 within the derrick 14. The swivel 24 is suspended from a traveling block 26, which in turn is connected through one or more cables 28 to a crown block 30 at the top of the derrick 14. The drill stem 22 extends downwardly through the marine riser 18 through the sea bed 16 and into a bore hole 32. A bit 34 is secured to the lower end of the drill stem 22. Rotation of the drill stem 22 and the bit 34 by conventional mechanical means (not shown) drills the borehole 32 in the earth.

Drilling fluid or mud is pumped from a mud tank 36 on the platform 10 by a mud pump 38 through a stand pipe 40 to the swivel 24. The mud is circulated down the hollow bore 23 of the drill stem 22 and out one or more ports 42 in the drill bit 34. The mud returns to the platform 10 through an annular space 44 between the drill stem 22 and the walls of the bore hole 32 and between the drill stem 22 and the interior walls of the marine riser 18. At the platform 10 the mud returns to the mud tank 36 through a mud return pipe 46. The mud performs several functions, including cooling and lubricating the bit 34, carrying away drilling debris, and maintaining a hydrostatic pressure balance against the geopressures of the surrounding earth formations in order to prevent any fluids which may be trapped in these earth formations from entering the borehole 32.

The apparatus which comprises the present invention is represented schematically in FIG. 1 by a sensor package 48 which is attached to the riser 18 most advantageously at a location just above the blowout preventor stack 20. The sensor package 48 is connected by a data link 50 to a control console 52 on the platform 10. The sensor package 48 contains the instrumentation for the measurement of mud/gas mass ratio and mud flow velocity, as well as instrumentation for the measurement of temperature, pressure, etc., as will be presently described.

The theory of operation of the mud/gas ratio sensor is based upon the behavior of the speed of sound (c) in a mixture of fluids. For the purposes of this invention, both drilling mud and gas may be properly considered fluids since neither substance will support a shear stress. The speed of sound in mud itself as a fluid is determined largely by the porosity of the mud, i.e., the volumetric proportion of interstitial liquid to solid matter. For porosities greater than about 0.5, the speed of sound is almost exactly that of the surrounding liquid. Normal drilling muds, with densities up to about twenty pounds per gallon, will thus behave as fluids acoustically.

The speed of sound in mud has a nominal value of approximately 1,600 meters per second. As gas is added to the mud, the speed of sound through the mixture will decrease from the nominal value since the speed of sound in any gas is much lower than 1,600 meters per second. The precise value of the speed of sound c in the mixture depends upon the type and quantity of gas present, and the temperature and pressure of the mixture, and is given by the following equation:

$$c^2 = \frac{c_1^2 c_2^2 (\gamma \rho_2 + \rho_1)^2}{(1 + \gamma)(\gamma \rho_2^2 c_2^2 + \rho_1^2 c_1^2)}, \quad (1)$$

$c_1$ = speed of sound in mud;
$\rho_1$ = density of mud;
$c_2$ = speed of sound in gas;
$\rho_2$ = density of the gas; and
$\gamma$ = the ratio of mud mass to gas mass in a fixed volume.

The quantities $\rho_1$, $\rho_2$, $c_1$, and $c_2$ can either be directly measured or deduced from auxiliary measurements as will be discussed presently. The theory of operation is therefore to measure c and then to compute $\gamma$ with the above equation.

Figure 2:
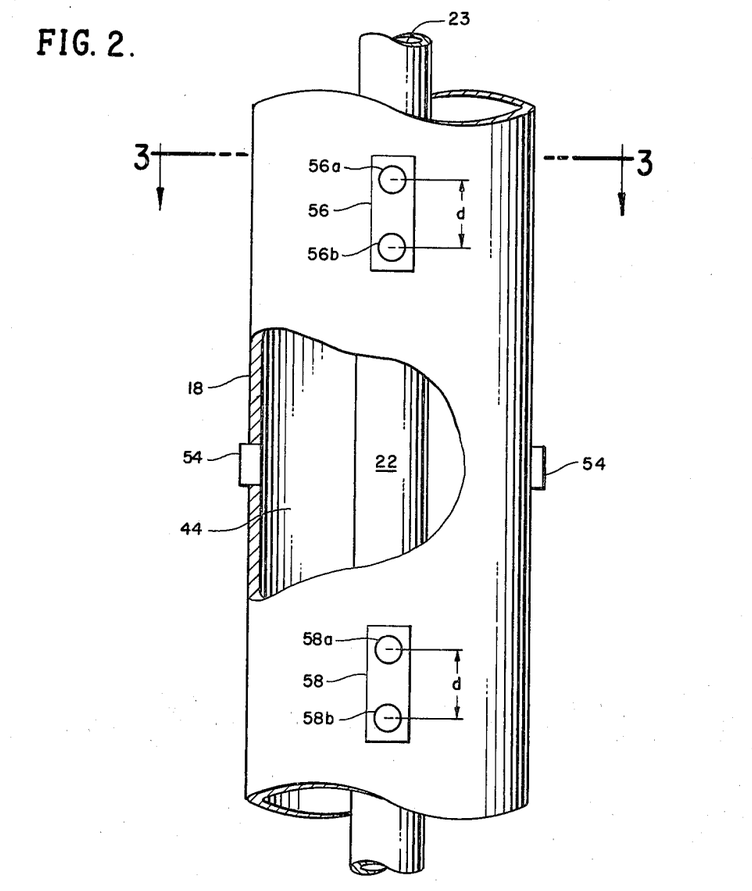
FIG. 2 is an elevational view, partially in section, of a portion of a riser on which the acoustical components of the present invention are mounted.
Figure 3:
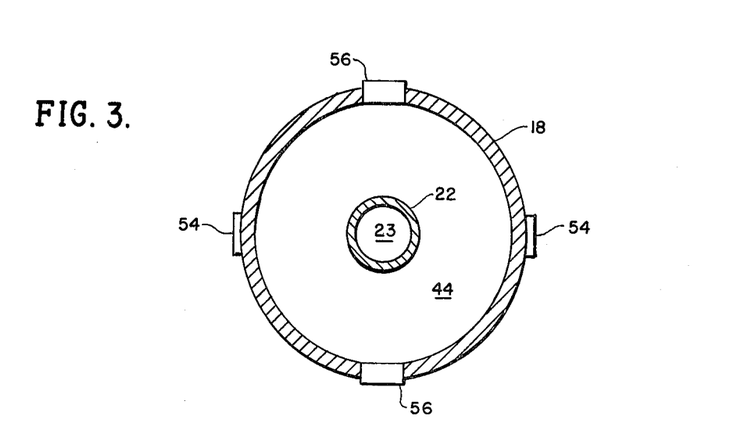
FIG. 3 is a cross-sectional view taken along line 3—3 of FIG. 2.

The measurement of c is accomplished acoustically. Referring to FIGS. 2 and 3, a pair of diametrically opposed acoustical projectors 54 are mounted in the riser 18 so as to be flush with the interior wall of the riser. Similarly mounted in the riser at a location above the projectors 54 is a pair of diametrically opposed downstream acoustical receiver arrays 56. The downstream receiver arrays 56 are rotated 90 degrees on the riser 18 from the projectors 54 so as to avoid acoustical interference by the drill stem 22. Each of the downstream receiver arrays comprises an upper receiver 56a vertically spaced a distance d from a lower receiver 56b. Similarly mounted on the riser 18 below the projectors 54 and likewise rotated 90 degrees with respect thereto is a pair of diametrically opposed upstream acoustical receiver arrays 58 comprising an upper receiver 58a vertically spaced a distance d above a lower receiver 58b. The projectors 54 and the receivers 56a, 56b, 58a and 58b may be conventional omni-directional piezo-electric transducers of the type adapted for use under water.

The above-described arrangement of the projectors 54 and receiver arrays 56 presents several significant advantages. The flush-mounting of the acoustical components eliminates any turbulence in the mud flow which would be induced by the protrusion of the components into the annular space 44, where interference with the mud flowing therein would occur. Such turbulence could distort the measurement of c, as well as the measurement of the mud flow velocity, which will be presently described. Moreover, the flush-mounting minimizes the chance of damage to the acoustical components from striking by the drill stem 22, which, under the stresses of drilling, can flex to a considerable degree, bringing a portion thereof into close proximity with the interior wall of the riser 18. Such flexing of the drill stem 22 may also bring a portion of the drill stem into a position where it would acoustically block or partially block one of the receiver arrays 56 and/or one of the projectors 54. The use of diametrically opposed pairs of the acoustical components provides at least one clear acoustical path if such blocking occurs, thereby allowing the measurement of c to be carried on uninterrupted.

Figure 4:
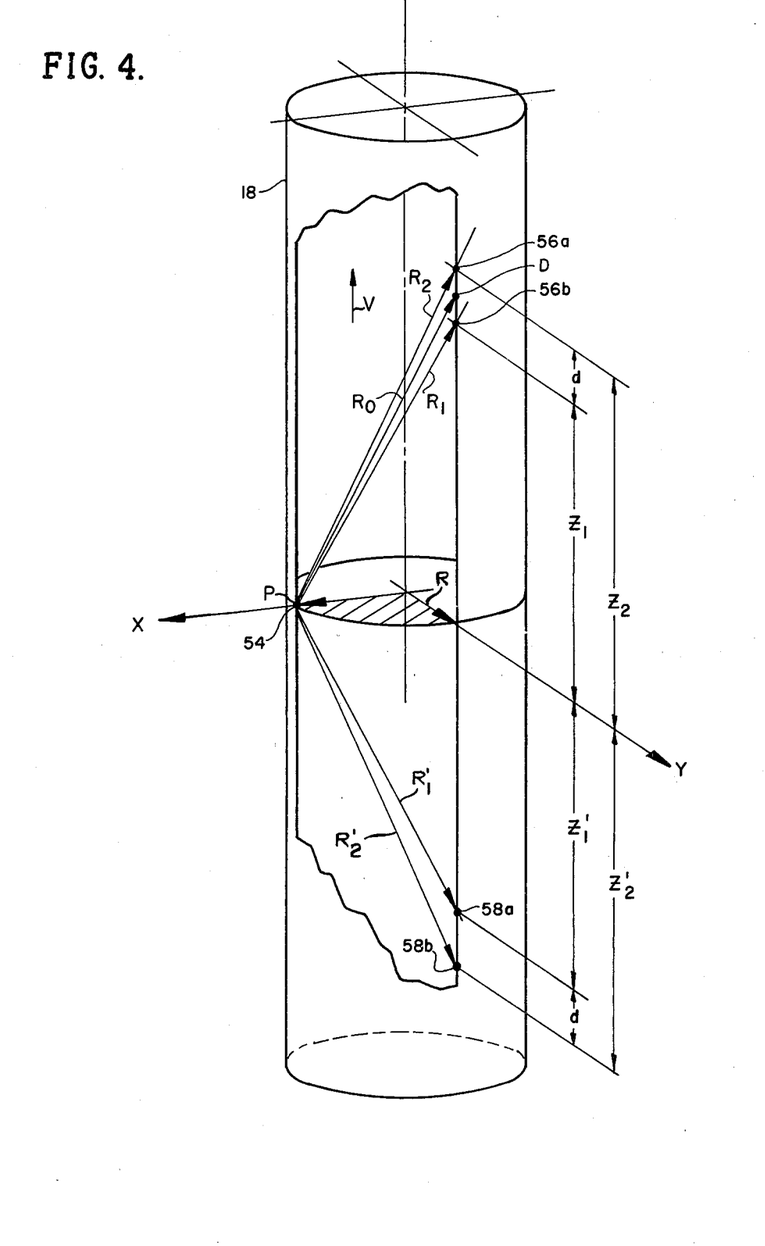
FIG. 4 is a diagramatic representation showing the specific spatial relationship among the acoustic components on the riser.

FIG. 4 illustrates schematically the critical spacing of the acoustical components in the riser 18. For purposes of simplification, only one each of the projectors 54, the downstream receiver arrays 56 and the upstream receiver arrays 58 are represented in FIG. 4. The projector 54 is located at point P in the riser and projects an acoustical wave within the riser and through the mud therein. The wave is received by the downstream receiver array 58 at locations 58a and 58b at distances $R_2$ and $R_1$ from the point P, corresponding to the locations of the upper and lower receivers 58a and 58b respectively. The locations $R_2$ and $R_1$ are vertically spaced from the point P by the vertical distances $Z_2$ and $Z_1$ respectively. $Z_1$ and $Z_2$ are chosen so that $Z_1 = [(n-\frac{1}{2})^2\lambda^2 - 2R^2]^{\frac{1}{2}}$, and $Z_2 = [(n+\frac{1}{2})^2\lambda^2 - 2R^2]^{\frac{1}{2}}$, where n is a predetermined number, preferably an integer;

$\lambda$ equals a nominal wave length for the projected accoustical wave; and

R equals the radial distance along the Y axis, of the points 56a and 56b from the longitudinal axis of the riser.

With this spacing, the phase center of the receiver array 56 will be at a point D located at a distance $R_0$ from the projector 54, where $R_0 = \frac{1}{2}(R_1 + R_2) = n\lambda$. Thus, the output from the receivers will be in a known phase relationship (180° out of phase) with the input to the projector if the frequency f of the projected wave is chosen so that given the relationship of the equation $$(f\lambda)/c = 1, \qquad (2)$$

$\lambda$ maintains the value such that the distance $R_0$ between the projector 54 and the phase center of the receiver array 56 remains $n\lambda$.

Figure 5:
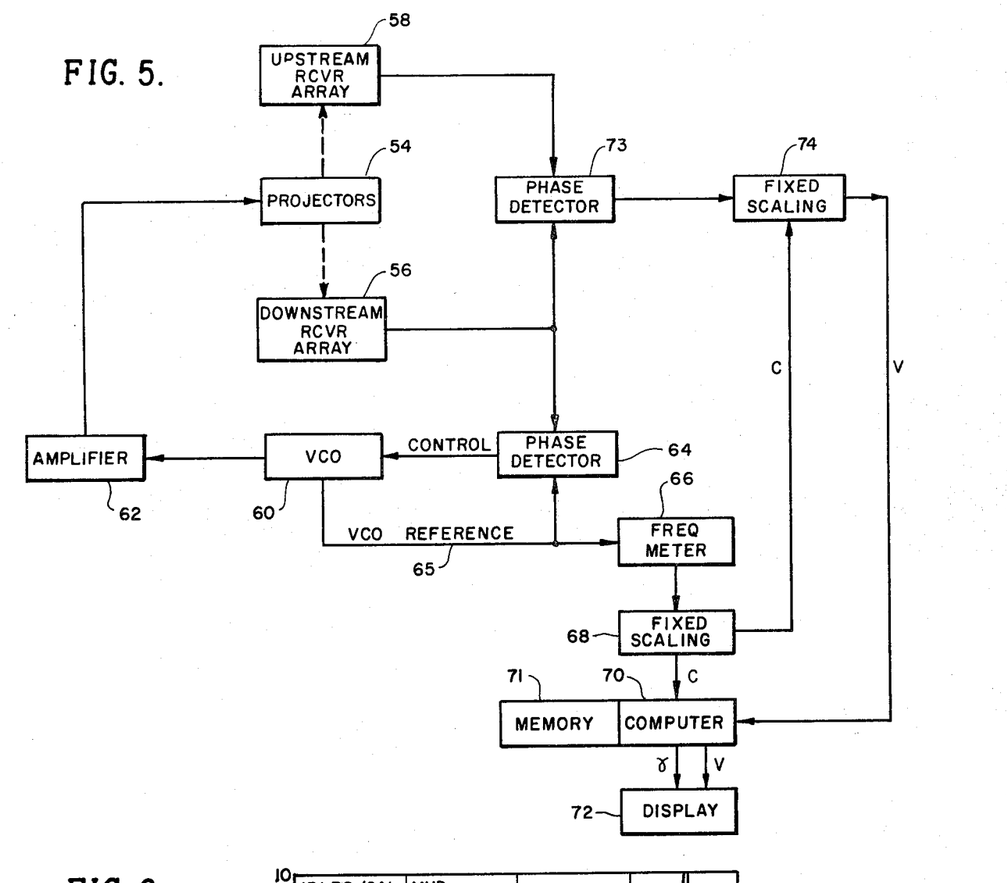
FIG. 5 is a schematic representation of the system used in the present invention.

The output of the receivers will thus remain in a known phase relationship with the input to the projector if, whenever c changes, f is changed so as to maintain $n\lambda$ in the distance $R_0$. Accordingly, to keep this relationship, a phase locked loop is used, as shown in FIG. 5.

The phase locked loop comprises a voltage controlled oscillator (VCO) 60 which drives an amplifier 62 which in turn powers the projectors 54. The acoustic wave produced by the projectors 54 is received by the downstream receiver arrays 56 and is converted into an electrical signal. This signal from the downstream receiver arrays 56 is fed into a phase detector 64 where the phase of this signal is compared to the phase of a reference signal 65 from the VCO 60. If the signal from the downstream receiver array 56 and the reference signal 65 from the VCO are in the desired phase relationship, it indicates that the relationship $n\lambda = R_0$ has been maintained and the phase detector 64 will yield an output signal having a predetermined voltage. However, if the two signals are out of phase, indicating that the relationship $n\lambda = R_0$ has not be maintained, the phase detector 64 will send a control signal having a voltage differing from said predetermined voltage by a voltage which is proportional to this difference in phase, to the VCO 60, causing the VCO 60 to change the frequency of its output signal until it is in the desired phase relationship with the signal from the downstream receiver arrays. The frequency of the VCO output signal is measured by a frequency meter 66, and it is directly proportional to c, since $\lambda$ is a function only of the mechanical spacing between the acoustic components. Specifically, $\lambda = R_2 - R_1$. Because of this proportionality, the frequency of the VCO output signal can be approximately scaled to produce a value for c by means of a fixed scaling circuit 68 which receives the value of f from a signal from the frequency meter 66 to produce a value for c.

The value of c thus measured will actually be slightly greater than the actual value of c due to the velocity V of mud flow, so that $c = V + c'$, where c' is the actual speed of sound and c is the measured speed of sound. However, since c' is two or three orders of magnitude greater than V, the error is insignificant, and c is essentially equal to c'.

The value of c derived from the fixed scaling circuit 68 is inputted into a mini-computer 70 having a memory 71 for the calculation of $\gamma$ by means of Equation 1. In calculating $\gamma$, the computer uses a statistical estimater for c which not only handles the various uncertainties in the problem but also provides predictions for future values. One particularly advantageous algorithm for producing such an estimate is that which is commonly known as a recursive Kalman filter estimater, in which the rate of change in the speed of sound in the drilling fluid is modeled as a zero mean random variable with an exponential auto-correlation function. This is equivalent to the intuitive notion that the mud/gas mass ratio is nominally an unknown constant, but that it might at any instant be growing or decreasing, and that its rate of change is limited as if through a low pass filter. The details of this algorithm are well-known. See, for example Roberts, *Signal Processing Techniques,* Interstate Electronics Corporation, Anaheim, California (1977) (pages 8-1 to 8-28). The theory behind the algorithm which is not a part of the present invention, may be briefly outlined as follows:

Given a sequence of measurements of a quantity (in this case the speed of sound c) which are assumed to be "noisy", or of uncertain accuracy, one desires to make an estimate of the true value. Commonly one accumulates a few values and averages them to obtain a better estimate. The Kalman filter produces an estimate equivalent to or better than averaging, and does it recursively, which makes it more atrractive for real time process control. The central idea is contained in the formula for the estimate:

$$\hat{c}(k) = \hat{c}_k(k-1) + K[c(k) - \hat{c}_k(k-1)]$$

where:
$\hat{c}(k)$ = best estimate of c at time (k), the desired result;
$\hat{c}_k(k-1)$ = best estimate of c at time (k−1), projected to measurement time (k) by known relationships.
$c(k)$ = measured value of c at time (k)
K = the Kalman weighting factor Note that if K=0, then $\hat{c}(k)$ is the projected value and measured values are ignored. If K=1, previous estimates are ignored and the measured value is taken as the best estimate. Intermediate values of K give weight more or less to predictions or to measured values. In the Kalman filter, K is recursively computed, based upon the statistics of the observed values of c, to give the best estimate of the quantity c, taking into account its uncertainty.

The best estimate of the value of c, obtained by the Kalman filter algorithm, is then used by the computer 70 to compute $\gamma$ by means of Equation 1. The value of $\gamma$ is then transmitted from the computer 70 to a visual display 72 in the control console 52 on the platform 10 by means of the data link 50.

While it is contemplated that the computer 70 will be programmed with an algorithm for the solution of Equation 1 for $\gamma$, it is also possible to provide a hardwired circuit, using conventional electronic components, to yield the solutions for $\gamma$. If Equation 1 is rewritten, in classical quadratic form, as:

$$\begin{aligned}&\gamma^2(c_1^2 c_2^2 \rho_2^2 - \rho_2^2 c_2^2 c^2) + \\ &\gamma(2\rho_1 \rho_2 c_1^2 c_2^2 - \rho_2^2 c_2^2 c^2 - \rho_1^2 c_1^2 c^2) + \\ &(c_1^2 c_2^2 \rho_1^2 - \rho_1^2 c_1^2 c^2) = 0,\end{aligned} \qquad (1a)$$

then the solutions for $\gamma$ may be obtained by means of the circuitry schematically illustrated in FIGS. 7A, 7B, 7C, and 7D.

Figure 7A:
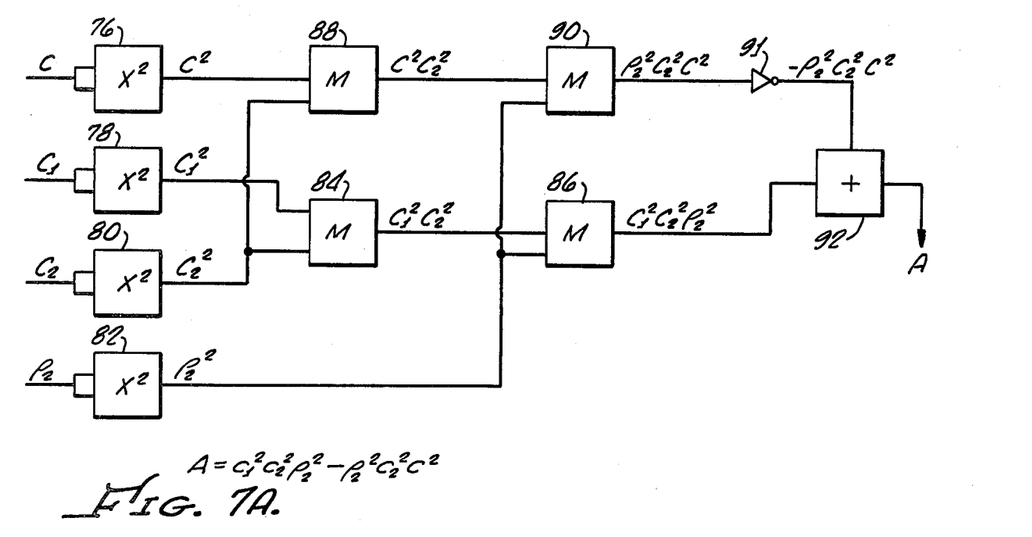
FIGS. 7A, 7B, 7C and 7D are schematic diagrams of the circuitry used to compute the mud/gas mass ratio.

The coefficient of the quadratic term in Equation 1a may be termed "A" and is computed by the circuit of FIG. 7A. Signals correspond to the values of c, $c_1$, $c_2$, and $\rho_2$ are inputted to squaring circuits 76, 78, 80, and 82, respectively. The squaring circuits 78 and 80 yield signals corresponding to $c_1^2$ and $c_2^2$ respectively, which are inputted to a multiplier circuit 84, which yields a signal corresponding to $c_1^2c_2^2$. This signal is inputted to a multiplier circuit 86 along with the $\rho_2^2$ signal from the squaring circuit 82 to yield a signal corresponding to $c_1^2c_2^2\rho_2^2$, the minuend of the quadratic coefficient. The $c_2^2$ signal from the squaring circuit 80 is also inputted to a multiplier 88 along with the $c^2$ signal from the squaring circuit 76 to yield a $c^2c_2^2$ signal, which, in turn, is inputted to a multiplier 90 with the $\rho_2^2$ signal to yield a $\rho_2c_2^2c^2$ signal. This signal is passed through an inverter 91, and then inputted to a summing circuit 92 along with the $c_1^2c_2^2\rho_2^2$ signal to yield a signal corresponding to A.

Figure 7B:
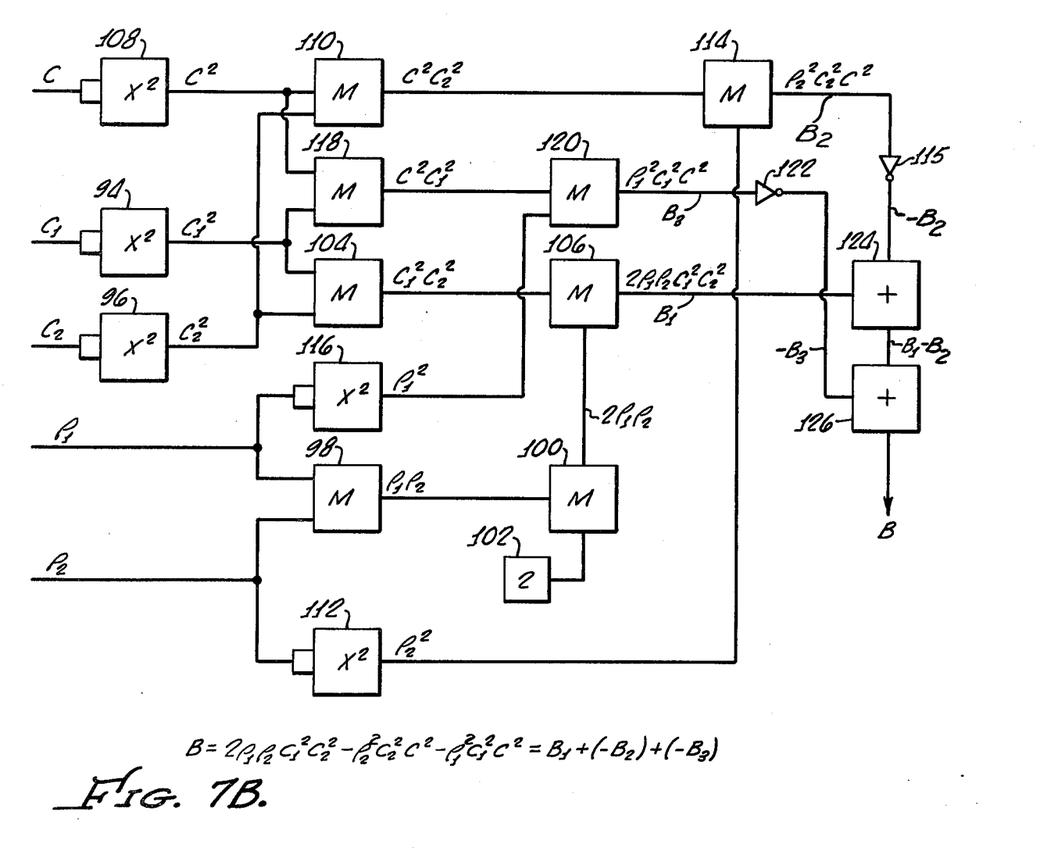

The coefficient of the first order term in Equation 1a may be called "B" and is computed by the circuit of FIG. 7B. Let us denote the first, second, and third terms of B as $B_1$, $B_2$, and $B_3$ respectively. $B_1$, then, is obtained as follows:

Signals corresponding to the values of $c_1$ and $c_2$ are inputted to squaring circuits 94 and 96 respectively, yielding signals corresponding to $c_1^2$ and $c_2^2$, respectively. Signals corresponding to the values of $\rho_1$ and $\rho_2$, respectively, are inputted to a multiplier 98 to yield a $\rho_1\rho_2$ signal. The $\rho_1\rho_2$ signal is inputted to multiplier 100 along with a signal corresponding to the value "2" from a "2" register 102 in the memory 71. The output from the multiplier 100 is, therefore, $2\rho_1\rho_2$. The $c_1^2$ and $c_2^2$ signals are inputted to multiplier 104 to yield a $c_1^2c_2^2$ signal, which is then inputted to a multiplier 106 along with the $2\rho_1\rho_2$ signal to yield a signal corresponding to $B_1$.

$B_2$ is obtained as follows: A signal corresponding to the value of c is squared by a squaring circuit 108 to yield a $c_2$ signal. This signal is inputted to a multiplier 110 along with the $c_2^2$ signal from the multiplier 96 to yield a $c_2^2c^2$ signal. The $\rho_2$ signal is inputted to a squaring circuit 112 to yield a $\rho_2^2$ signal. The $\rho_2$ signal and the $c^2c_2^2$ signal are inputted to a multiplier 114 to yield $B_2$, which is made negative by an inverter 115 to yield $-B_2$.

$B_3$ is obtained as follows: The $\rho_1$ signal is squared by a squaring circuit 116 to yield a $\rho_1^2$ signal. The $c_1^2$ and $c^2$ signals are inputted to a multiplier 118 to yield a $c^2c_1^2$ signal, which is inputted to a multiplier 120 with the $\rho_1^2$ signal to yield $B_3$. The $B_3$ signal is then inverted by an inverter 122 to yield $-B_3$.

The $B_1$ and $-B_2$ signals are inputted to a summing circuit 124 to yield a $B_1-B_2$ signal, which is inputted to a second summing circuit 126 with the $-B_3$ signal to yield B.

Figure 7C:
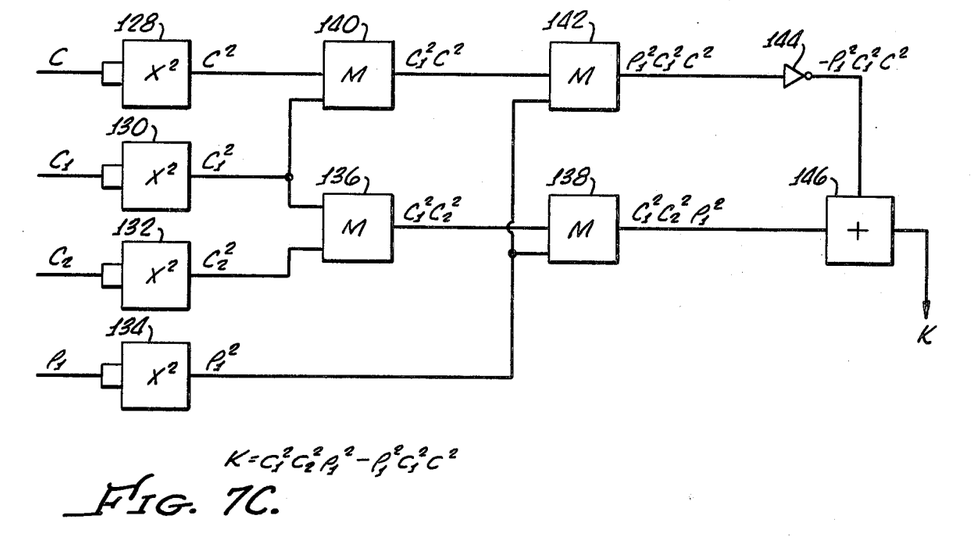
Figure 7D:
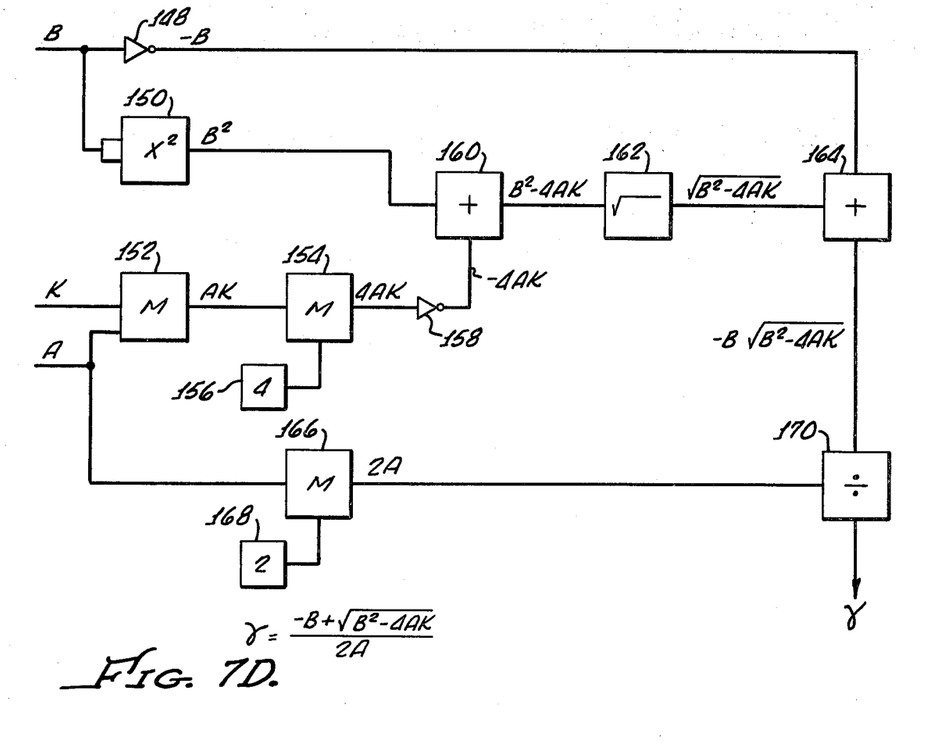

The constant term in Equation 1a $(c_1^2c_2^2\rho_1^2-\rho_1^2c_1^2c^2)$ may be called "K" and is computed by the circuit of FIG. 7C. Signals corresponding to the values of c, $c_1$, $c_2$, and $\rho_1$ are squared by squaring circuits 128, 130, 132, and 134, respectively, to yield $c^2$, $c_1^2$, $c_2^2$ and $\rho_1^2$. The $c_1^2$ and $c_2^2$ signals are inputted to a multiplier 136 to yield a $c_1^2c_2^2$ signal, which, in turn, is inputted to a multiplier 138 with the $\rho_1^2$ signal to yield $c_1^2c_2^2\rho_1^2$. The $c^2$ and $c_1^2$ signals are inputted to a multiplier 140 to yield a $c_1^2c^2$ signal, which, in turn, is inputted to a multiplier 142 with the $\rho_1^2$ signal to yield $\rho_1^2c_1^2c^2$. The $\rho_1^2c_1^2c^2$ signal is inverted by an inverter 144 to yield a $-\rho_1^2c_1^2c^2$ signal, which is inputted to a summing circuit 146 with the $c_1^2c_2^2\rho_1^2$ signal to yield K.

The solution of Equation 1a (and therefore, of Equation 1) for $\gamma$ is given by the quadratic formula:

$$\gamma = \frac{-B \pm \sqrt{B^2 - 4AK}}{2A} \tag{1b}$$

For our purposes, we need only consider one root of the formula 1b, which may be considered to be the root given by using $+\sqrt{B^2-4AK}$. Using this formula, the solution for $\gamma$ is obtained by the circuit of FIG. 7D, as follows.

A signal corresponding to the value of B obtained from the circuit of FIG. 7B is inverted by an inverter 148 to yield $-B$. The B signal is also inputted to a squaring circuit 150 to yield $B^2$. Signals corresponding to the values of K and A obtained from the circuits of FIGS. 7C and 7A, respectively, are inputted to a multiplier 152 to yield an AK signal. This latter signal is inputted to a multiplier 154 along with a signal corresponding to the value "4" obtained from a "4" register 156 in the memory 71. The resulting signal, corresponding to 4AK, is inverted by an inverter 158 to yield $-4AK$. The $-4AK$ signal is inputted to a summing circuit 160 along with the $B^2$ signal to yield a $(B^2-4AK)$ signal, which then inputted to a square-root circuit 162 to yield $\sqrt{B^2-4AK}$. This latter signal is inputted to a summing circuit 164 along with the $-B$ signal to produce the numerator in the formula 1b. The denominator of the formula is produced by taking the signal corresponding to the value of A and inputting it into a multiplier 166 along with a signal representing the value "2" from a "2" register 168 in the memory 71 to yield a signal corresponding to 2A. This latter signal is inputted into a divider circuit 170 along with the numerator signal from the summing circuit 164 to yield the value of $\gamma$.

The functions of the circuits illustrated in FIGS. 7A, 7B, 7C and 7D may be carried out by equivalent circuits which will be apparent to those skilled in the art. Furthermore, the multiplying, squaring, summing, inverting, dividing, and square-root-taking circuits shown in FIGS. 7A, 7B, 7C and 7D are all well known in the art, and are readily available, for example, in the form of integrated circuits.

In order to calculate $\gamma$ it is, of course, necessary to know the values of the parameters used in Equation 1.

The value of the mud density parameter $\rho_1$ at the sensor site may be closely approximated by measuring the returning mud at the drilling platform by any of several known methods. Most commonly, a known volume of the returned mud is simply weighed. In recent years, more sophisticated methods have been devised, one such method being disclosed in U.S. Pat. No. 3,839,914, to Modisette et al. The value for $\rho_1$ obtained at the platform is a good approximation to the value at the sensor site because typical amounts of gas cutting will measurably change the speed of sound c while not appreciably changing the mud density. In other words, Equation 1 is relatively insensitive to variations in the mud density $\rho_1$. For this reason, the initial density of the mud introduced into the well can also be used as a reasonable approximation of the value of $\rho_1$. However determined, the value of $\rho_1$ can be stored in the memory 71.

The value of the gas density parameter $\rho_2$ is related to the temperature and density of the gas at the sensor site by the relation given by the following equation:

$$\rho_2 = (P_2/T_2)(T_o/P_o)\rho_o \tag{3}$$

where $T_o$ and $P_o$ are standard temperature (absolute) and pressure, respectively; $T_2$ and $P_2$ are temperature (absolute) and pressure, respectively, at the sensor site; and $\rho_o$ is the gas density at standard temperature and pressure $(T_o, P_o)$.

$T_o$, $P_o$, and $\rho_o$ are known constants which can be stored in the memory 71. $T_2$ and $P_2$ can be measured directly at the sensor site by conventional means, such as thermistors and pressure transducers, which can be conveniently incorporated into the sensor package 48. These measured values are then inputted to the computer 70 for the computation of $\rho_2$.

The speed of sound $c_1$ in pure drilling mud of a given initial density is a function of the pressure and the temperature at the sensor site. If the speed of sound in mud at standard temperature (absolute) and pressure is $c_{o1}$, then:

$$c_1 = c_{o1} + 0.019h + 3.12(T - T_o) \quad (4)$$

where h equals sensor depth (meters) and T equals the temperature (°K.) at the sensor site, and $T_o$ is standard temperature (°K.). The term 0.019h is a previously determined correction factor incorporating the fact that the pressure at the sensor site is a known function of depth. The term $3.12(T - T_o)$ is a predetermined correction factor for the effect of temperature on the speed of sound. The sensor site temperature T can be measured, as previously discussed, and the sensor depth is a known constant for a given well and can be stored in the memory along with $T_o$. The value of $c_{o1}$ is also a known constant which can be stored in the memory 71. Thus, the value of T can be inputted to the computer 70 for the calculation of $c_1$ by Equation 4.

The speed of sound in gas is a function of the temperature at the sensor site, and is given by the equation:

$$c_2 = c_{o2}\sqrt{T/T_o} \quad (5)$$

where $c_{o2}$ is the speed of sound in the gas at standard temperature (absolute) and pressure; T is the temperature at the sensor site (°K.) and $T_o$ is standard temperature (°K.). The sensor site temperature T again is measurable, and $T_o$ is stored in the memory 71, as previously discussed. For any given gas, $c_{o2}$ is also a known constant which can be stored in the memory 71. Thus, the measured value of T can be inputted to the computer 70 for the calculation of $c_2$.

Since the values of $c_{o2}$ and $\rho_o$ are different for different types of gas, the values of $c_2$ and $\rho_2$ will vary, depending on the type of gas that is present in the mud at the sensor site. However, initially, the type of gas is not known, so the computer 70 is advantageously programmed to start out with the values of $c_{o2}$ and $\rho_o$ corresponding to methane, which is the most likely gas to be encountered. When the composition of the gas is determined as by analyzing samples of returned mud on the platform with a gas spectrometer, the operator can signal the computer from the control console 52 to use previously stored values of $c_{o2}$ and $\rho_o$ corresponding to the specific type of gas encountered.

Figure 6:
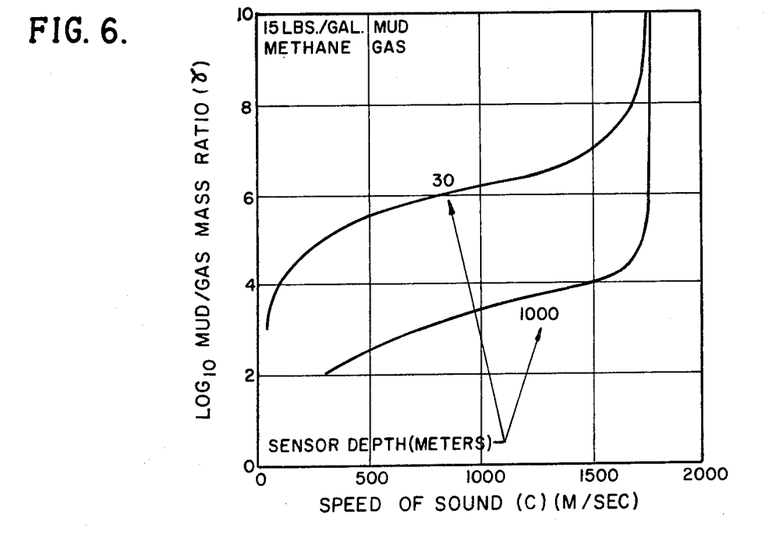
FIG. 6 is a graphical representation of log 10 of the mud/gas mass ratio as a function of the speed of sound in a mud/gas mixture for typical conditions.

Referring to FIG. 6, typical curves of $\log_{10}\gamma$ as a function of c are given for typical conditions. As can be seen from FIG. 6, the value of $\log_{10}\gamma$ varies linearly with c over a broad range. For example, for a sensor depth of 1,000 meters, the curve is essentially linear for values of $\gamma$ from approximately 100 to 10,000. For a sensor depth of 30 meters, the curve is approximately linear for values of $\gamma$ ranging from about $10^5$ to $10^7$.

For relatively shallow sensor depths, the density of mud is approximately 1,000 times the density of gas. Thus, referring to the curve corresponding to a sensor depth of 30 meters in FIG. 6, a value of $\gamma$ of $10^6$ would indicate a volumetric ratio of gas to mud of approximately 1,000 to 1. Volumetric ratios of mud to gas greater than or equal to this ratio are usually considered to be within the normal operating range. On the other hand, if $\gamma$ is determined to be significantly less than $10^6$, an abnormally high level of gas cutting is indicated, signalling an impending kick. Therefore, corrective measures would be instituted upon the taking of such a reading of $\gamma$. Thus, the linear portion of this curve is advantageously used for the monitoring of conditions at or near the normal operating range.

For sensor depths approaching 1,000 meters, the density of mud is typically less than 100 times the density of gas. Thus, for the curve corresponding to a sensor depth of 1,000 meters, measurements of $\gamma$ which fall on the linear portion of the curve would indicate dangerously low volumetric ratios of mud to gas, signalling a level of gas cutting which would be indicative of a strong blowout potential.

The above discussion illustrates the desirability, in deep water drilling installations, of having two sensors: a shallow sensor to monitor conditions at or near the expected operating range; and a deep sensor to give an early warning of dangerous conditions.

The curves in FIG. 6 have been drawn for an initial mud density of 15 pounds per gallon, which is typical in most drilling applications. A variation from this initial density would alter the curve somewhat; therefore, the computer 70 is advantageously programmed to receive the initial mud density value as an input for the computation of $\gamma$. Moreover, appropriate scaling factors can be incorporated into the computer algorithm to quantify the mud/gas ratio in terms of any desired units, such as, for example, milliliters of gas per liter of mud or grams of gas per kilogram of mud.

A particular advantage of the present invention is its convenient adaptability to function as a phase shift velocimeter to measure the velocity of flow of mud in the riser. The monitoring of this parameter is desirable in drilling operations, since the striking by the drill of formations containing abnormally pressurized fluids will result in an increased rate of flow of the mud returning up the riser, and this effect of increasing the rate of flow will travel up the riser at approximately the speed of sound. Therefore, the measurement of an increased mud flow rate through the riser is a very prompt indication of an impending kick. Moreover, the mud flow velocity is responsive not only to gas cutting of the mud, but also to the cutting of the mud by liquids, particularly water. Thus, the inclusion in the sensor package of a phase shift velocimeter gives the invention an added flexibility and utility at relatively little expense in terms of additional hardware and software. Moreover, since the measurement of mud flow velocity with a phase-shift velocimeter is dependent on the value of the speed of sound c, as will be presently described, the accuracy of the velocimeter incorporated in the present invention is greatly enhanced by the use of the accurate values of c which are derived from the mud/gas ratio sensor, thereby eliminating the necessity for using estimated values for c.

It is for the purposes of the phase shift velocimeter function that the upstream receiver array 58, as shown in FIG. 2, is incorporated into the invention. The principle of the phase shift velocimeter is well known (see, for example, U.S. Pat. No. 3,861,211 to Dewan) and is illustrated schematically in FIG. 4. Mud flows upwardly through the riser 18 with a velocity V indicated by the arrow V. The receivers 58a and 58b in the upstream receiver array 58 are located on the riser at points 58a and 58b which are distances $R_1'$ and $R_2'$ respectively from the projector 54. As shown in FIG. 4, the locations 58a and 58b are vertically spaced downwardly from the point P (the projector location) by the vertical distances $Z_1'$ and $Z_2'$ respectively. The distances $Z_1'$ and $Z_2'$ are equal to the distances $Z_1$ and $Z_2$ of the downstream receiver array 56, so that the arrangement of the upstream receiver array 58 with respect to the projectors 54 is the mirror image of the arrangement between the downstream receiver array 56 and the projectors 54, with the distances $R_1'$ and $R_2'$ being respectively equal to $R_1$ and $R_2$.

As previously described, the downstream receiver array 56 is locked into phase with the projectors 54 by means of the phase locked loop, so as to determine the value of c used in the calculation of $\gamma$. However, due to the effects of the mud velocity V, the acoustic wave received at the upstream receiver array 58 is lagging in phase the wave received by the downstream receiver array by approximately $4pR_oV/\lambda c$ radians where $R_o = \frac{1}{2}(R_1+R_2) = n\lambda$, as previously described.

The derivation of the above approximation for the phase lag may be briefly described as follows:

The actual phase lag ($\Delta\phi$) is given by the following equation:

$$\Delta\phi = 2\pi\left(\frac{fR_o}{c+V} - \frac{fR_o}{c-v}\right) \quad (6)$$

The wavelength $\lambda$ equals c/f. However, as previously discussed, c is really equal to c+V when the speed of sound is measured between the projector 54 and the downstream receiver array 56. Thus, $\lambda$ will equal (c=V)/f. Thus, Equation 6 becomes $$\Delta\phi = 2\pi\left(\frac{R_o}{\lambda} - \frac{fR_o}{c-V}\right) \quad (6a)$$

But $R_o=n\lambda$, so the equation becomes $$\Delta\phi = 2\pi\left(n - \frac{fR_o}{c-V}\right) \quad (6b)$$

By algebraic manipulation, Equation 6b can be written as:

$$\Delta\phi = 2\pi n\left(\frac{2Vn/fR_o}{1 - 2Vn/fR_o}\right) \quad (6c)$$

However, the term $2Vn/fR_o$ will be very much smaller than 1 for appropriately chosen values of n, $R_o$, and f, so that Equation 6c can be approximated as $$\Delta\phi = 4\pi Vn^2/fR_o \quad (6d)$$

If f is approximated as c/$\lambda$, then the equation becomes:
$$\Delta\phi = 4\pi Vn^2\lambda/cR_o \quad (6e)$$

But $n^2=R_o^2/\lambda^2$ so that Equation 6e can be written as:
$$\Delta\phi = 4\pi VR_o/\lambda c \quad (6f)$$

, which has been found to be a very close approximation of Equation 6. The mud flow velocity is therefore given by the equation:

$$V = \lambda c\Delta\phi/4\pi R_o \quad (7)$$

Referring now to FIG. 5, the receivers 58a and 58b convert the acoustic wave into an electrical signal which has a corresponding phase lag as compared to the signal produced by the downstream receiver array 56. The signals from the upstream receiver array 58 and the downstream receiver array 56 are fed into a second phase detector 73, which measures the difference in phase between the upstream receiver array signal and the downstream receiver array signal. This phase difference is proportional to V/C since $\lambda$ and $R_o$ are fixed. Because of this proportionality, the phase difference can be approximately scaled to produce a value for V by means of a second fixed scaling circuit 74 which receives the value of the phase difference from the second phase detector 73 and the value of C from the first fixed scaling circuit 68. The value of V from the second fixed scaling circuit 74 is subject to various uncertainties, due, for example, to axial variations in the mud flow and swirl induced by the drill stem 22. In order to reduce these uncertainties, it is advantageous to feed the values of V from the second fixed scaling circuit 74 into the computer 70 so that the recursive Kalman filter estimator algorithm may produce a best estimate of V, as previously described with regard to the measurement of c. The value of V is then transmitted via the data link 50 to the display 72 in the control console 52.

Thus, with the system described above, the well operator can obtain accurate and continuous measurements of the amount of gas present in the mud, while at the same time obtaining a measurement of the mud flow velocity, the accuracy of which is enhanced by the use of the accurate values of the speed of sound which are obtained by the mud/gas mass ratio sensor system.

What is claimed is:

1. A device for the sensing of drilling fluid properties in a well-drilling operation, comprising:
    a riser through which said drilling fluid passes;
    acoustic projector means mounted in said riser for projecting an acoustic wave through said drilling fluid, said acoustic wave having a predetermined wavelength $\lambda$ and a frequency f;
    first acoustic receiver means mounted in said riser for receiving said acoustic wave, said first acoustic receiver means having a phase center which is spaced from said acoustic projector means by a distance equal to a predetermined number of said wavelengths $\lambda$;
    means for locking said first acoustic receiver means into a predetermined phase relationship with said acoustic projector means by changing said frequency f of said acoustic wave so as to maintain said predetermined number of said wavelengths $\lambda$ in said distance when the speed of sound c through said drilling fluid changes in response to a change in the amount of gas in said drilling fluid;
    metering means electronically coupled to said phase-locking means for measuring said frequency f and producing a signal;
    first electronic scaling means responsive to said signal from said metering means, for calculating said speed of sound c and producing a signal indicative of said speed of sound c;

computing means responsive to said signal from said first scaling means, for calculating a ratio $\gamma$ of drilling fluid mass to gas mass, using an equation $$c^2 = \frac{c_1^2 c_2^2 (\gamma \rho_2 + \rho_1)^2}{(1 + \gamma)(\gamma \rho_2^2 c_2^2 + \rho_1^2 c_1^2)},$$

where $c_1$ is the speed of sound in pure drilling fluid, $c_2$ is the speed of sound in gas, $\rho_1$ is the density of pure drilling fluid, and $\rho_2$ is the density of gas;

second acoustic receiver means mounted in said riser for receiving said acoustic wave, said second receiver means having a phase shift with respect to said first receiver means due to a flow velocity of said drilling fluid, said phase shift being approximately proportional to said drilling fluid flow velocity and inversely proportional to said speed of sound c through said drilling fluid;

phase detector means electronically coupled to said first and second receiver means for measuring said phase shift and producing a signal; and second electronic scaling means, responsive to said signal from said phase detector means and said signal from said first scaling means, for calculating said drilling fluid flow velocity.

2. The device of claim 1, wherein said projector means and said first and second receiver means are electro-acoustical transducers, and said projector transducer is driven at said frequency f by a voltage-controlled oscillator.

3. The device of claim 2 wherein said phase locking means is a phase-locked loop, comprising:
said voltage-controlled oscillator;
a signal from said first receiver means;
a frequency reference signal from said voltage-controlled oscillator; and
phase detecting means for comparing the phase of said frequency reference signal with the phase of said signal from said first receiver means and producing an output signal having a voltage which is proportional to the difference in phase between said frequency reference signal and said signal from said first receiver means, said voltage-controlled oscillator responding to said output signal by shifting said frequency reference signal until said output signal has a predetermined voltage.

4. The device of claim 1, wherein said first and second receiving means each comprise a pair of vertically spaced transducers, one of said pair being a distance of $(n+\frac{1}{2})\lambda$ from said projector means, and the other of said pair being a distance of $(n-\frac{1}{2})\lambda$ from said projector means, where n is a predetermined number.

5. The device of claim 4, wherein said first and second receiving means are rotated 90° on said riser from said projector means.

6. A device for measuring the amount of gas present in a drilling fluid used in drilling a well, comprising:
a riser through which said drilling fluid flows;
acoustic projector means mounted in said riser for projecting an acoustic wave through said drilling fluid, said acoustic wave having a pre-determined wavelength $\lambda$ with an associated frequency f, said wave being produced in response to an electrical input signal to said projector means;
acoustical receiver means mounted in said riser downstream from said projector means for receiving said acoustic wave and converting said wave into an electrical output signal, said receiver means having a phase center spaced from said projector means by a distance equal to a predetermined number of said wavelengths $\lambda$;

means for locking said output signal into a predetermined phase relationship with said input signal by varying said input signal to change said frequency f of said projected acoustic wave so as to maintain said predetermined number of said wavelengths $\lambda$ in said distance when the speed of sound c through said drilling fluid changes in response to a change in the amount of gas in said drilling fluid;

metering means electronically coupled to said phase-locking means for measuring said frequency f and producing a signal;

electronic speed of sound scaling means responsive to said signal from said metering means for calculating said speed of sound c and producing a signal indicative of said speed of sound c; and computing means responsive to said signal from said scaling means, for calculating a ratio $\gamma$ of drilling fluid mass to gas mass, using an equation $$c^2 = \frac{c_1^2 c_2^2 (\gamma \rho_2 + \rho_1)^2}{(1 + \gamma)(\gamma \rho_2^2 c_2^2 + \rho_1^2 c_1^2)},$$

where $c_1$ is the speed of sound in pure drilling fluid, $c_2$ is the speed of sound in gas, $\rho_1$ is the density of pure drilling fluid, and $\rho_2$ is the density of gas.

7. The device of claim 6, further comprising mud flow velocity measuring means responsive to said signal from said scaling means.

8. The device of claim 7, wherein said mud flow velocity measuring means comprises:
a second acoustic receiver means mounted in said riser upstream from said projector means for receiving said acoustic wave from said projector means and producing a second output signal having a phase shift with respect to said input signal due to a flow velocity of said drilling fluid, said phase shift being approximately proportional to said flow velocity and inversely proportional to said speed of sound c;
phase detector means for measuring said phase shift and producing a signal having a voltage proportional to said phase shift; and
flow velocity scaling means responsive to said signal from said phase detector means and to said signal from said speed of sound scaling means for calculating said flow velocity.

9. A method of measuring the relative proportions of drilling fluid and gas in a mixture of drilling fluid and gas flowing upwardly in a riser from the bottom of a well, comprising the steps of:
determining the speed of sound $c_1$ in pure drilling fluid;
determining the speed of sound $c_2$ in gas;
determining the density $\rho_1$ of pure drilling fluid;
determining the density $\rho_2$ of gas;
measuring the speed of sound c in said mixture; and
computing a ratio $\gamma$ of drilling fluid mass to gas mass with the equation $$c^2 = \frac{c_1^2 c_2^2 (\gamma \rho_2 + \rho_1)^2}{(1 + \gamma)(\gamma \rho_2^2 c_2^2 + \rho_1^2 c_1^2)}.$$

10. The method of claim 9, where said step of measuring of said speed of sound c in said mixture comprises the steps of:

projecting an acoustic wave of wavelength $\lambda$ and frequency f from an acoustic projector in said riser;

receiving said acoustic wave by an acoustic receiver located in said riser a distance which is predetermined number of said wavelengths $\lambda$ from said projector;

locking said acoustic receiver in a predetermined phase relationship with said projector by changing said frequency f of said acoustic wave so as to maintain said predetermined number of said wavelengths $\lambda$ in said distance when said speed of sound c through said mixture changes in response to a change in the amount of gas in said mixture;

measuring said frequency f which maintains said predetermined number of said wavelength $\lambda$ in said distance; and calculating said speed of sound c by using a relationship $f\lambda/c = 1$.

11. In a well-drilling operation in which drilling fluid is pumped up and out of a bore-hole through a riser, and in which said riser has mounted therein an acoustic projector, a first acoustic receiver downstream from said projector, and a second acoustic receiver upstream from said projector, a method of measuring the amount of gas mixed with said drilling fluid and the flow velocity of said drilling fluid, comprising the steps of:

projecting an acoustic wave through said drilling fluid and gas mixture from said projector in response to an electrical input signal to said projector, said wave having a wavelength $\lambda$, a predetermined number of which equals the distance from said projector to said first receiver, said wavelength $\lambda$ having an associated frequency f;

receiving said wave by said first and second receivers;

converting said wave into a first electrical output signal from said first receiver;

locking the phase of said first output signal into a predetermined phase relationship with the phase of said input signal by changing said frequency f of said acoustic wave so as to maintain said predetermined number of said wavelengths $\lambda$ in said distance when the speed of sound c in said drilling fluid changes in response to a change in the amount of gas in said drilling fluid and gas mixture;

measuring said frequency f which maintains said predetermined number of said wavelengths $\lambda$ in said distance;

calculating said speed of sound c by using a relationship $f\lambda/c = 1$;

computing a ratio $\gamma$ of drilling fluid mass to gas mass in said mixture with an equation $$c^2 = \frac{c_1^2 c_2^2 (\gamma \rho_2 + \rho_1)^2}{(1 + \gamma)(\gamma \rho_2^2 c_2^2 + \rho_1^2 c_1^2)}$$

where $c_1$, $c_2$, $\rho_1$, and $\rho_2$ are pre-determined values of the speed of sound in drilling fluid, speed of sound in gas, density of drilling fluid, and density of gas, respectively;

converting said acoustic wave into a second electrical output signal from said second receiver;

measuring the difference in phase between said first output signal and said second output signal, said difference in phase being approximately proportional to the flow velocity v of said drilling fluid through said riser and inversely proportional to said speed to cound c through said drilling fluid and gas mixture; and using the previously calculated value of the speed of sound c through the drilling fluid and gas mixture to calculate the value of said flow velocity v.

12. The method of claim 11, further comprising the steps of:

predicting future values of said ratio $\gamma$ by using a statistical estimator for said equation.

13. The method of claim 12, wherein said statistical estimator is a recursive Kalman filter estimator algorithm.

14. A method of predicting blowouts during the drilling of a well in which a drilling fluid is used, wherein the amount of gas mixed with said drilling fluid is an indicator of blowout potential, comprising the steps of:

acoustically measuring the speed of sound in said mixture of drilling fluid and gas in said well;

obtaining a best estimate of the value of the speed of sound; and computing the mass ratio of drilling fluid to gas based upon said best estimate of the value of the speed of sound.

15. The method of claim 14, wherein said measuring step comprises the steps of:

conducting said mixture upwardly from the bottom of said well through a riser;

projecting an acoustic wave of a predetermined wavelength into said riser and the mixture flowing therein;

receiving said wave at a first location after said wave has traveled a distance equal to a predetermined number of said wavelengths;

adjusting the frequency of said projected acoustic wave so as to maintain said predetermined number of wavelengths in said distance when the speed of sound in said mixture changes in response to a change in the proportions of drilling fluid and gas in said mixture;

measuing the frequency which maintains said predetermined number of wavelengths in said distance; and calculating the value of the speed of sound based upon the measured frequency and said predetermined wavelength.

16. The method of claim 15, further comprising the steps of:

receiving said wave at a second location;

comparing the phase of said wave received at said first and second locations;

measuring a phase shift based upon said comparison; and computing the flow velocity of said mixture based upon said measured phase shift and said calculated value of the speed of sound.

17. The method of claim 14, wherein said best estimate is obtained by applying a statistical estimator for said measured values.

18. The method of claim 14 further comprising the step of computing the flow velocity of said mixture base upon said measured speed of sound.

19. Apparatus for computing the mass ratio of drilling fluid and gas in a well riser, comprising:

first means for acoustically measuring the speed of sound in a mixture of drilling fluid and gas in said well; and second means responsive to said first means for computing said ratio based upon said measured speed of sound.

20. The apparatus of claim 19, further comprising third means responsive to said first means for computing the flow velocity of said mixture based upon said measured speed of sound.

21. The apparatus of claim 20, wherein said first means comprises:

projector means for projecting an acoustic wave through said mixture;

first receiver means at a first location for receiving said wave and producing a first signal; and second receiver means at a second location for receiving said wave and producing a second signal.

22. The apparatus of claim 21, wherein said third means comprises:

means for measuring a phase shift between said first and second signals resulting from the velocity of flow of said mixture between said first and second receiver means; and means responsive to said measuring means for calculating said velocity of flow based upon said measured value of the speed of sound and said measured phase shift.

23. The apparatus of claim 19, wherein said first means comprises:

projector means for projecting an acoustic wave into said riser and through said mixture of drilling fluid and gas therein, said wave having a predetermined wavelength;

receiver means at a distance from said projector means equal to a fixed number of said wavelengths;

frequency-varying means coupled to said projector means and said receiver means for maintaining said fixed number of wavelengths in said distance by varying the frequency of said wave as the speed of sound through said mixture changes in response to a change in the relative proportions of drilling fluid and gas in said mixture;

metering means responsive to said frequency-varying means for measuring the frequency which maintains said fixed number of wavelengths in said distance; and electronic scaling means responsive to said metering means for calculating the speed of sound based upon said measured frequency and said predetermined wavelength.

24. The apparatus of claim 19, wherein said second means comprises:

estimator means for obtaining a best estimate among several measured values of the speed of sound; and calculating means for computing said ratio based upon said best estimate of said measured values of the speed of sound.

25. The apparatus of claim 24, wherein said second means is a computer and said estimator means and said calculating means are computer algorithms.

* * * * *